US008444964B2

(12) United States Patent
Habib et al.

(10) Patent No.: US 8,444,964 B2
(45) Date of Patent: *May 21, 2013

(54) COMPOSITIONS AND METHODS FOR ENHANCED TUMOR CELL IMMUNITY IN VIVO

(75) Inventors: Fakhrai Habib, La Jolla, CA (US); Dorigo Oliver, San Diego, CA (US); Sobol E Robert, La Jolla, CA (US)

(73) Assignee: Novarx, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/192,952

(22) Filed: Jul. 11, 2002

(65) Prior Publication Data

US 2002/0192199 A1 Dec. 19, 2002

Related U.S. Application Data

(63) Continuation of application No. 09/516,737, filed on Mar. 1, 2000, now Pat. No. 6,447,769, which is a continuation of application No. 08/968,986, filed on Nov. 12, 1997, now Pat. No. 6,120,763, which is a continuation of application No. 08/276,694, filed on Jul. 18, 1994, now Pat. No. 5,772,995.

(51) Int. Cl.
*C12N 5/09* (2010.01)
*C12N 5/10* (2006.01)
*C07H 21/00* (2006.01)

(52) U.S. Cl.
USPC ...................... 424/93.21; 536/24.5

(58) Field of Classification Search
USPC ................ 424/93.21; 435/320.1, 455; 800/4, 800/21; 536/24.5
See application file for complete search history.

(56) References Cited

U.S. PATENT DOCUMENTS

| | | | |
|---|---|---|---|
| 5,637,483 | A | 6/1997 | Dranoff et al. |
| 5,681,562 | A | 10/1997 | Sobol et al. |
| 5,731,144 | A | 3/1998 | Toothman et al. |
| 5,772,995 | A | 6/1998 | Fakhrai et al. |
| 6,120,763 | A | 9/2000 | Fakhrai et al. |
| 2003/0147867 | A1* | 8/2003 | Fakhrai ...................... 424/93.21 |

FOREIGN PATENT DOCUMENTS

| | | |
|---|---|---|
| EP | EP 0 695 354 B1 | 9/2002 |
| WO | WO 94/25588 | 11/1994 |
| WO | WO 95/07105 | 3/1995 |
| WO | WO 96/02143 | 2/1996 |

OTHER PUBLICATIONS

Leslie Pray, The Scientist 16, 13:34, 2002.*
Yingling, Nature Reviews, vol. 3, 1011-1022, 2004.*
Arca et al., "Diverse manifestations of tumorigenicity and immunogenicity displayed by the poorly immunogenic B16-BL6 melanoma transduced with cytokine genes," *Cancer Immunol. Immonother.* 42:237-245 (1996).
Bodmer et al., "Human glioblastoma cell derived transforming growth factor-β2: evidence for secretion of both high and low molecular weight biologically active forms," *J. Neuroimmun.* 34:33-42 (1991).
Brabletz et al., "Transforming growth factor β and cyclosporin a inhibit the inducible activity of the interleukin-2 gene in t cells through a noncanonical octamer-binding site," *Mol. Cell. Biol.* 13:115-162 (1993).
Gilboa, "Immunotherapy of cancer with genetically modified tumor vaccines," *Seminars in Oncology* 1(23):101-107 (1996).
Gold, L., "The role for transforming growth factor-β (TGF-β) in human cancer," Crit. Rev. Oncog., 10(4):303-360 (1999).
Gridley et al., "Effects of anti-transforming growth factor-β antibody and interleukin-2 in tumor-bearing mice," *Cancer Biother.* 8:159-170 (1993).
Hanks et al., "Amino acids sequence of the BSC-1 cell growth inhibitor (polyergin) deduced from the nucleotide sequence of the cDNA," *Proc. Natl. Acad. Sci. USA.* 85:79-82 (1988).
Hirte et al., "Reversal of suppression of lymphokine-activated killer cells by transforming growth factor-β in ovarian carcinoma ascitic fluid requires interleukin-2 combined with anti-CD3 antibody," *Cell. Immunol.* 142:207-216 (1992).
Hirte and Clark, "Generation of lymphokine-activated killer cells in human ovarian carcinoma ascitic fluid: identification of transforming growth factor-β as a suppressive factor," *Cancer Immunol. Immunother.* 32:296-302 (1991).
Inge et al., "Inhibition of tumor-specific cytotoxic T-lymphocyte responses by transforming growth factor $\beta_1$," *Cancer Res.* 52: 1386-1392 (1992).
Jachimczak et al., "The effect of transforming growth factor-β-specific phosphorothioate-anti sense oligodeoxynucleotides in reversing cellular immunosuppression in malignant glioma," *J. Neurosurg.* 78:944-951 (1993).
Kuppner et al., "Inhibition of lymphocyte function by glioblastoma-derived transforming growth factor β2," *J. Neurosurg.* 71:211-217 (1989).
Lord et al., "Transfection of TGF-β producing tumors with IL-2 elicits tumor rejection," *Annals of the New York Academy of Sciences* 690:346-348 (1993).
Mastrangelo et al., "Gene therapy of human cancer: an essay for clinicians," *Seminars in Oncology* 1(23):4-21 (1996).
Riddell et al., T-cell mediated rejection of gene-modified HIV-specific cytotoxic T lymphocytes in HIV-infected patients, *Nature Medicine* 2(2):216-223 (1996).
Rosenberg et al., "Gene transfer into human-immunotherapy of patients with advanced melanoma, using tumor-infiltrating lymphocytes modified by retroviral gene transduction," *New Engl. J. Med.* 323:570-578 (1990).
Ruffini et al., "Factors, including transforming growth factor β, released in the glioblastoma residual cavity, impair activity of adherent lymphokine-activated killer cells," *Cancer Immunol.* 36:409-416 (1993).

(Continued)

*Primary Examiner* — Anne Marie S Wehbe
(74) *Attorney, Agent, or Firm* — Morrison & Foerster LLP

(57) ABSTRACT

The invention provides a method of preventing or reducing the severity of a cancer in a subject by stimulating the subject's immune response against the cancer. The invention provides, for example, a method of stimulating an immune response in a subject by administering to the subject tumor cells that are substantially similar to the subject's cancer cells and that are genetically modified to reduce or inhibit the expression of one or more immunosuppressive agents. The invention also provides a method of preventing or reducing the severity of cancer in a subject by stimulating the subject's immune response against the cancer by administering to the subject tumor cells that are substantially similar to the subject's cancer cells and that are genetically modified to prevent the expression of an immunosuppressive agents and, in combination with the genetically modified tumor cells, an immunostimulatory agent. The invention further provides compositions useful for practicing the claimed methods.

9 Claims, 2 Drawing Sheets

OTHER PUBLICATIONS

Sulitzeanu, Dov, "Immunosupressive factors in human cancer," *Adv. Cancer Res.* 60:247-267 (1993).

Spearman et al, "Antisense oligodeoxyribonucleotide inhibition of TGF-β1 gene expression and alterations in the growth and malignant properties of mouse fibrosarcoma cells." *Gene* 149:25-29 (1994).

Tepper and Mule, "Experimental and clinical studies of cytokine gene-modified tumor cells," *Human Gene Therapy* 5:153-164 (1994).

Weiskirch et al., "Transforming growth factor-β-mediated down-regulation of antitumor cytotoxicity of spleen cells form MOPC-315 tumor-rearing mice engaged in tumor eradication following low-dose melphalan therapy," *Cancer Immun.* 38:215-224 (1994).

Wu et al., "Repression of autocrine transforming growth factor $β_1$ and $β_2$ in quiescent CBS colon carcinoma cells leads to progression of tumorigenic properties," *Cell Growth & Diff* 4:115-123 (1993).

Wu et al, "TGF-β1 is an autocrine-negative growth regulator of human colon carcinoma FET cells in vivo as revealed by transfection of an antisense expression vector." *J. Cell Biology* 116: 187-196 (1992).

Yamamoto et al., "TGF-β mediates natural suppressor activity of IL-2-activated lymphocytes," *J. Immunology* 3824-3847 (1994).

Dranoff et al, "Vaccination with irradiated tumor cells engineered to secrete murine granulocyte-macrophage colony-stimulating factor stimulates potent, specific, and long-lasting anti-tumor immunity," *Proc. Natl. Acad. Sci. USA* 90:3539-3543 (1993).

Mao et al, "Immunotherapy with Low-dose Interleukin-2 and Anti-transforming Growth Factor-β Antibody in a Murine Tumor Model," *Cancer Biotherapy* 9:317-327 (1994).

Pardoll, Drew, "Immunotherapy with cytokine gene-transduced tumor cells: the next wave in gene therapy for cancer," *Current Opinion in Oncology* 4:1124-1129 (1992).

Jachimczak et al., "The effect of transforming growth factor-$β_2$-specific phosphorothioate-anti-sense oligodeoxynucleotides in reversing cellular immunosuppression in malignant glioma," *J Neurosurg*, 78:944-951 (1993).

* cited by examiner

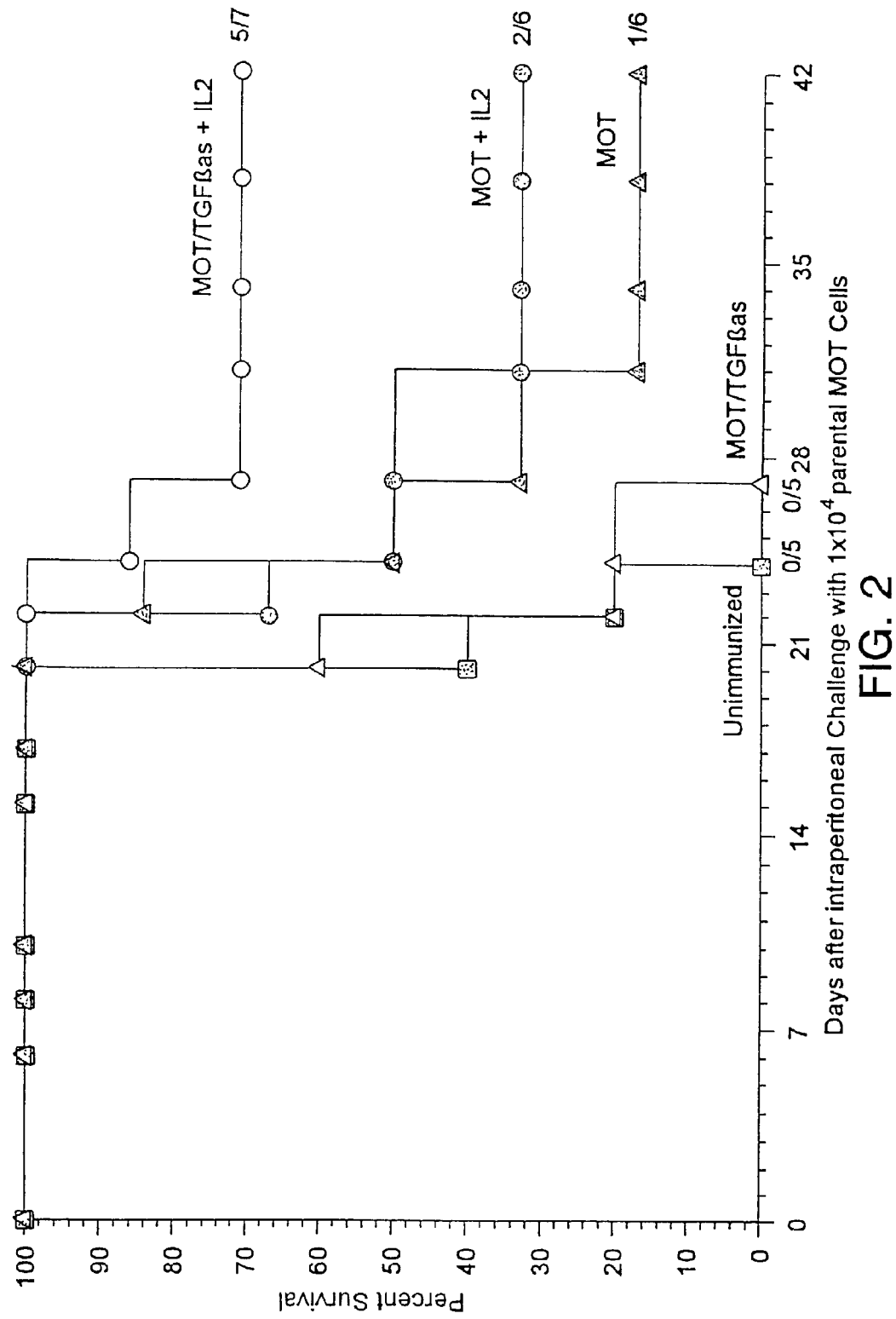

COMPOSITIONS AND METHODS FOR ENHANCED TUMOR CELL IMMUNITY IN VIVO

This application is a continuation of application Ser. No. 09/516,737, filed Mar. 1, 2000, now U.S. Pat. No. 6,447,769, which is a continuation of application Ser. No. 08/968,986, filed Nov. 12, 1997, now U.S. Pat. No. 6,120,763, which is a continuation of application Ser. No. 08/276,694, filed Jul. 18, 1994, now U.S. Pat. No. 5,772,995.

BACKGROUND OF THE INVENTION

1. Field of the Invention

The present invention relates generally to anti-tumor vaccines and, more particularly, to the use of gene therapy to augment immunological functions in response to anti-tumor vaccines.

2. Background Information

Recent advances in our understanding of the biology of the immune system have lead to the identification of cytokines as important modulators of immune responses. Cytokines produced by lymphocytes are termed lymphokines. These agents mediate many of the immune responses to tumors. Several cytokines have been produced by recombinant DNA methodology and evaluated for their anti-tumor effects.

The administration of lymphokines and related immunomodulators has produced some positive responses in patients with various types of neoplasms. However, current cytokine administration is frequently associated with toxic effects that limit the therapeutic value of these agents. For example, interleukin-2 (IL-2) is an important lymphokine in the generation of anti-tumor immunity. In response to tumor antigens, a subset of lymphocytes, helper T cells, secrete a small amount of IL-2, which acts locally at the site of tumor antigen stimulation to activate cytotoxic T cells and natural killer cells that mediate systemic tumor cell destruction.

In addition to immunostimulatory agents such as cytokines, which positively regulate immune effector functions, there also exist molecules that exhibit immunosuppressive activity. These immunosuppressive agents, if aberrantly regulated, can have detrimental effects on the induction of systemic immunity. For example, one or more isoforms of transforming growth factor-$\beta$ (TGF$\beta$) can be an immunosuppressive agent that is secreted by many tumor types. Culture supernatants from tumor cells that secrete an immunosuppressive form of TGF$\beta$ can reduce tumor specific cytotoxicity in vitro. In these in vitro cytotoxicity assays, inhibition of TGF$\beta$ activity by expression of antisense TGF$\beta$ can enhance tumor cell cytotoxicity.

Due, in part, to endogenous concentrations of immunosuppressive agents in a subject having a cancer, it cannot be predicted whether inhibiting the secretion of an immunosuppressive agent by the tumor cell will render the tumor cell immunogenic in vivo. For example, TGF$\beta$ secreted by cancer cells can circulate throughout a cancer patient and generally immunocompromise the patient. As a result, administration of tumor cells that are substantially similar to the patient's cancer cells and that are genetically modified to prevent the expression of an immunosuppressive agent would not necessarily be expected to stimulate the patient's immune response against the cancer cells. Similarly, the results of in vitro models of anti-tumor immune responses do not reliably predict the outcome of related immune system manipulations in vivo.

The modulation of cytokine concentrations has been attempted as a means to enhance a cancer patient's immune response toward target cancer cells. For example, intravenous, intralymphatic or intralesional administration of IL-2 has produced clinically significant responses in some cancer patients. However, severe toxic effects such as hypotension and edema limit the dose and efficacy of intravenous and intralymphatic IL-2 administration. The toxicity of systemically administered lymphokines is not surprising as these agents mediate local cellular interactions and normally are secreted only in very small quantities. In addition, intralesional administration of IL-2 can be difficult to accomplish and can cause significant patient morbidity.

To circumvent the toxicity of systemic cytokine administration, an alternative approach involving cytokine gene transfer into tumor cells has produced anti-tumor immune responses in several animal tumor models. In these studies, the expression of cytokines following cytokine gene transfer into tumor cells resulted in a reduction in tumorigenicity of the cytokine-secreting tumor cells when implanted into syngeneic hosts. Reduction in tumorigenicity occurred using IL-2, gamma-interferon or interleukin-4. In studies employing IL-2 gene transfer, the treated animals also developed systemic anti-tumor immunity and were protected against subsequent tumor cell challenges with unmodified parental tumor cells. Similar inhibition of tumor growth and protective immunity also was demonstrated when immunizations were performed with a mixture of unmodified parental tumor cells and tumor cells that were genetically modified to express IL-2. No toxicity was associated with localized lymphokine transgene expression in these animal studies.

Cytokines also have been expressed in heterologous cell types such as fibroblasts, which were coinjected into a cancer patient with the patient's own cancer cells. Coinjection of cytokine-expressing cells yielded a similar induction of systemic anti-tumor immunity as produced by cytokine-expressing tumor cells. Nevertheless, while these gene transfer procedures can provide significant anti-tumor immunity compared to other methods, a significant fraction of the patients do not respond optimally to such therapy. Thus, there exists a need to provide more effective methods to prevent or reduce the severity of a cancer in a patient. The present invention satisfies this need and provides related advantages as well.

SUMMARY OF THE INVENTION

The present invention provides a method of preventing or reducing the severity of a cancer in a subject by stimulating the subject's immune response against the cancer. For example, a cancer patient can be immunized with tumor cells that are substantially similar to the subject's cancer cells but that are genetically modified to prevent the expression of at least one immunosuppressive agent.

The invention also provides a method of stimulating a subject's immune response against a cancer by administering tumor cells that are substantially similar to the subject's cancer cells but that are genetically modified to prevent the expression of at least one immunosuppressive agent and to express at least one immunostimulatory agent such as a cytokine or a known tumor antigen. The invention further provides a method of stimulating a cancer patient's immune response against the cancer by co-administering to the subject an immunostimulatory agent such as an adjuvant, a cytokine or cytokine-expressing cells (CE cells), which are cells that are genetically modified to express a cytokine, and tumor cells that are substantially similar to the subject's cancer cells and that are genetically modified to prevent the expression of at least one immunosuppressive agent.

The invention also provides compositions useful for preventing or reducing the severity of a cancer in a subject by stimulating the subject's immune response against the cancer. A composition of the invention can contain tumor cells that are substantially similar to the subject's cancer cells and that are genetically modified to prevent the expression of at least one immunosuppressive agent. In addition, if desired, the genetically modified tumor cells can be further modified to express an immunostimulatory agent such as a cytokine or a known tumor antigen. A composition of the invention also can contain an immunostimulatory agent such as an adjuvant, a cytokine or CE cells and tumor cells that are substantially similar to the subject's cancer cells and that are genetically modified to prevent the expression of at least one immunosuppressive agent.

BRIEF DESCRIPTION OF THE DRAWINGS

FIG. 2 illustrates the effect of immunization on the survival of mice injected with murine ovarian teratoma (MOT) tumor cells. Mice were immunized with either unmodified MOT cells (MOT), MOT cells genetically modified to express antisense TGFβ (MOT/TGFβas), unmodified MOT cells and CE cells (MOT+IL2) or a combination of MOT cells genetically modified to express antisense TGFβ and CE cells (MOT/TGFβas+IL-2). Control mice were not immunized (Unimmunized). Numbers on the right indicate surviving mice/total mice tested.

DETAILED DESCRIPTION OF THE INVENTION

Figure 1B:
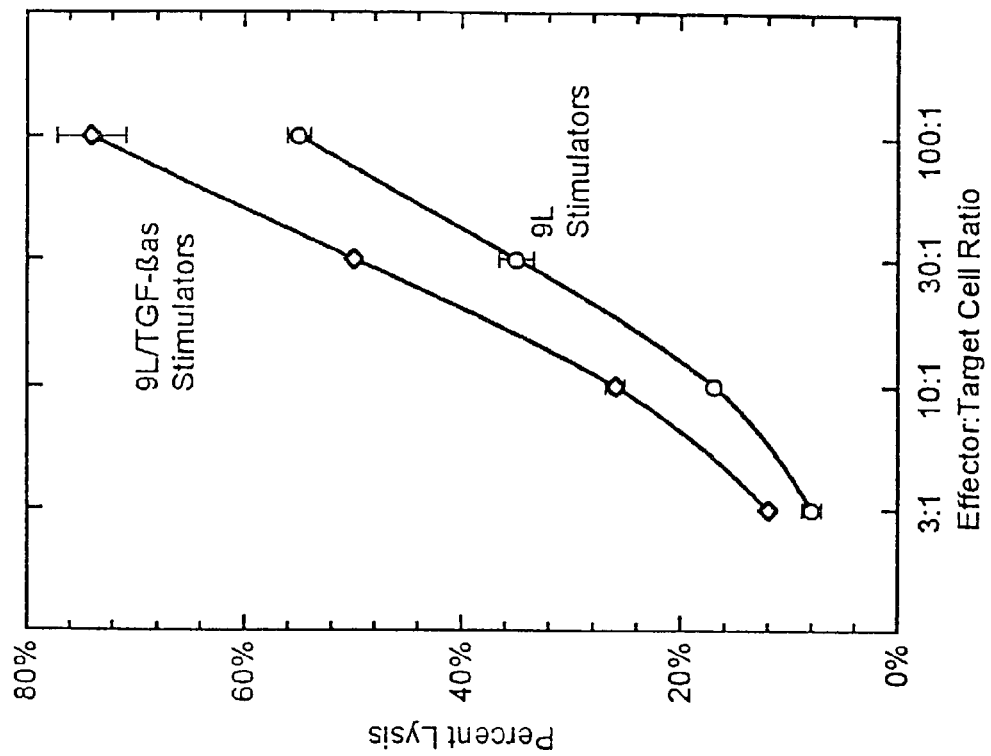
FIGS. 1.A. and 1.B. illustrate the in vitro anti-tumor lytic activity of lymph node effector cells from rats immunized with unmodified 9L gliosarcoma cells (FIG. 1.A.; 9L Immunized) or with 9L cells modified to express and secrete IL-2 (FIG. 1.B.; 9L/LNCX/IL-2 Immunized). Lymph node cells were harvested from immunized animals and stimulated in vitro in the presence of 50 BRMP units IL-2/ml medium with either unmodified 9L cells or 9L cells that were genetically modified to express an antisense TGFβ. Target cells consisted of unmodified 9L cells.

The present invention provides compositions that can effectively prevent or reduce the severity of a cancer in a subject and methods for using the compositions. In particular, the invention provides compositions containing tumor cells that are genetically modified to reduce or inhibit the expression of one or more immunosuppressive factors normally produced by the tumor cells. Tumor cells that produce immunosuppressive factors are known in the art and are present, for example, in carcinomas, sarcomas, gliomas, melanomas, lymphomas and leukemias (Sulitzeanu, Adv. Canc. Res. 60:247-267 (1993), which is incorporated herein by reference). Whether a cancer is producing an immunosuppressive agent can be readily determined using methods as described herein or otherwise known in the art.

A composition of the invention contains tumor cells that are genetically modified to provide an enhanced systemic immune response against a cancer by preventing or reducing the expression of one or more immunosuppressive agents by the tumor cells. It is recognized, therefore, that prior to genetic modification, the tumor cells are characterized, in part, by their ability to express an immunosuppressive agent.

A composition of the invention can contain the genetically modified tumor cells, alone, or in combination with an immunostimulatory agent such as a cytokine or cytokine-expressing cells (CE cells), which are cells that are genetically modified to express a cytokine. A composition of the invention also can contain tumor cells that are genetically modified to reduce or inhibit the expression of an immunosuppressive agent and are further genetically modified to express an immunostimulatory agent such as a cytokine or a known tumor antigen. The compositions of the invention are advantageous over existing cancer vaccines because the disclosed compositions, when administered to a subject, can provide superior modulation of the subject's immune functions.

As used herein, the term "preventing or reducing the severity of a cancer" means that the clinical signs or symptoms of the cancer in a subject are indicative of a beneficial effect to the subject due to stimulation of the subject's immune response against the cancer. The prevention of a cancer can be indicated by an increased time before the appearance of a cancer in a subject that is predisposed to developing a cancer. A subject can be predisposed to developing a cancer due, for example, to a genetic predisposition or to exposure to a carcinogenic agent. A reduction in the severity of a cancer can be indicated by a decrease in size or in growth rate of the tumor, which can be determined using various imaging methods. The prevention or reduction in the severity of a cancer also can be determined indirectly by detecting the activation of immunoeffector functions in a subject such as the activation of tumor cytolytic immunoeffector cells.

A composition of the invention can prevent or reduce the severity of a cancer by stimulating an immune response against the cancer. As used herein, the term "stimulating an immune response" means that an immune response is induced or that the activity of immunoeffector cells is enhanced in response to administration to a subject of a composition of the invention. Stimulation of an immune response can be indicated by comparing the immune functions of a subject prior to administration of a composition with the immune functions following administration. Immune functions can be determined using methods described below or otherwise known in the art for measuring a humoral or cellular immune response. Prevention or a reduction in the severity of a cancer as indicated by the methods described herein are an indication that the subject's immune response against the cancer has been stimulated.

In one embodiment, tumor cells are removed from a subject having a cancer, which is characterized, in part, by cancer cells that express at least one immunosuppressive agent such as an immunosuppressive isoform of TGFβ, and the tumor cells are genetically modified to reduce or inhibit the expression of the immunosuppressive agent. Methods for genetically modifying a cell are known in the art and described in detail below. Although the tumor cells to be genetically modified can be obtained from the subject to be treated, they also can be obtained from a source other than the cancer patient, provided the tumor cells are substantially similar to the subject's cancer cells and express an immunosuppressive agent. Tumor cells can be obtained from a source other than the subject to be treated if, for example, the subject's own tumor cells are not accessible or the subject is predisposed to, but does not yet have, cancer.

As used herein, the terms "tumor cell" and "cancer cell" are used interchangeably to mean a malignant cell. A tumor cell can occur in and can be obtained from a solid tumor such as a sarcoma, carcinoma, melanoma, lymphoma or glioma or a more diffuse cancer such as a leukemia. Tumor cells can be obtained from a subject having a cancer, from a donor subject having a cancer that is the same or substantially similar to the cancer in the subject to be treated or from a tumor cell repository. For convenience, the term "donor tumor cell" is used to mean tumor cells that are obtained from a source other than the subject to be treated.

It is recognized that a patient's cancer cells may or may not express an immunosuppressive agent. However, only if the patient's cancer cells express one or more immunosuppressive agents are the cancer cells genetically modified to reduce or inhibit the expression of the immunosuppressive agent(s). A subject's cancer cells that do not express an immunosuppressive factor can be genetically modified to express an immunostimulatory agent as described below.

As used herein, the term "tumor cells that are substantially similar to the subject's cancer cells" means tumor cells such as allogeneic tumor cells that are of the same or similar histologic type as the subject's cancer cells or that express a tumor specific or tumor associated antigen that is the same or similar to an antigen expressed by the subject's cancer cells. Such tumor antigens are known in the art (see, for example, Finn, *Curr. Opin. Immunol.* 5:701-708 (1993), which is incorporated herein by reference). For convenience of discussion, the subject's own tumor cells are considered to be within the meaning of this term. Allogenic tumor cells that are substantially similar to the subject's cancer cells can be identified, for example, using histological, histochemical, biochemical, molecular biological or immunological methods well known in the art.

As used herein, the term "immunosuppressive agent" refers to a gene product that has an inhibitory effect on the functions of the immune response. An immunosuppressive agent can interfere, for example, with the function of a cytokine or can inhibit or suppress the immune response by other mechanisms. Immunosuppressive agents are known in the art and include, for example, TGFβ, lymphocyte blastogenesis inhibitory factor, the retroviral p15E protein, suppressive E-receptor (see Sulitzeanu, supra, 1993) and extracellular matrix molecules such as fibronectin and tenascin (Olt et al., *Cancer* 70:2137-2142 (1992); Hemasath et al., *J. Immunol.* 152:5199-5207 (1994), each of which is incorporated herein by reference). It is recognized, for example, that various isoforms of TGFβ such as TGFβ1, TGFβ2, TGFβ3, TGFβ4 and TGFβ5 exist (see, for example, Roszman et al., *Immunol. Today,* 12:370-274 (1991); Constam et al., *J. Immunol.,* 148: 1404-1410 (1992); Elliot et al., *J. Neuro-Oncology,* 14:1-7 (1992), each of which is incorporated herein by reference) and that the immunosuppressive effect of one or more of these isoforms of TGFβ depends, for example, on the target cell. The term "TGFβ" is used generally herein to mean any isoform of TGFβ, provided the isoform has immunosuppressive activity.

As used herein, the term "express an immunosuppressive agent" means that the tumor cells produce an immunosuppressive agent. As used herein, the term "reduce or inhibit the expression of an immunosuppressive agent" is used in its broadest sense to mean that the level of an RNA molecule encoding an immunosuppressive agent or the level or activity of the immunosuppressive agent, itself, is reduced to a level that is less than the level expressed prior to the genetic modification. The terms "reduce" and "inhibit" are both used because, in some cases, the level of expression of an immunosuppressive agent can be reduced to a level that is below the level-detectable by a particular assay and, therefore, it cannot be determined whether expression of the immunosuppressive agent is reduced or is completely inhibited. Use of the term "reduce or inhibit" prevents any potential ambiguity due, for example, to the limitations of a particular assay.

Reduction or inhibition of expression of an immunosuppressive agent that is expressed by a tumor cell can be accomplished using known methods of genetic modification. For example, a tumor cell expressing an immunosuppressive agent such as an immunosuppressive isoform of TGFβ can be genetically modified such that the expression of the TGFβ is reduced or inhibited using a homologous recombination gene "knock-out" method (see, for example, Capecchi, *Nature,* 344:105 (1990) and references cited therein; Koller et al., *Science,* 248:1227-1230 (1990); Zijlstra et al., *Nature,* 342: 435-438 (1989), each of which is incorporated herein by reference; see, also, Sena and Zarling, *Nat. Genet.,* 3:365-372 (1993), which is incorporated herein by reference). The homologous recombination gene knock-out method provides several advantages. For example, expression of a gene encoding an immunosuppressive agent such as a TGFβ gene in a tumor cell can be inhibited completely if both alleles of the target gene are inactivated. In addition to providing complete inhibition of the immunosuppressive agent, the method of homologous recombination gene knock-out is essentially permanent.

The expression of an immunosuppressive agent by a tumor cell also can be reduced or inhibited by providing in the tumor cell an antisense nucleic acid sequence, which is complementary to a nucleic acid sequence or a portion of a nucleic acid sequence encoding an immunosuppressive agent such as an immunosuppressive isoform of TBFβ. Methods for using an antisense nucleic acid sequence to inhibit the expression of a nucleic acid sequence are known in the art and described, for example, by Godson et al., *J. Biol. Chem.,* 268:11946-11950 (1993), which is incorporated herein by reference. Expression of an immunosuppressive agent by a tumor cell also can be reduced or inhibited by providing in the tumor cell a nucleic acid sequence encoding a ribozyme, which can be designed to recognize and inactivate a specific mRNA such as a mRNA encoding an immunosuppressive isoform of TGFβ (see, for example, McCall et al., *Proc. Natl. Acad. Sci., USA,* 89:5710-5714 (1992); Cremisi et al., *Proc. Natl. Acad. Sci., USA;* 89:1651-1655 (1992); Williams et al., *Proc. Natl. Acad. Sci., USA,* 89:918-921 (1992); Neckers and Whitesell, *Amer. J. Physiol.* 265:L1-12 (1993); Tropsha et al., *J. Mol. Recoq.* 5:43-54 (1992), each of which is incorporated herein by reference).

The expression of an immunosuppressive agent by a tumor cell also can be reduced or inhibited by genetically modifying the tumor cell to express a binding protein that can bind the immunosuppressive agent and render it inactive. For example, the tumor cell can be genetically modified to express a natural receptor for the immunosuppressive agent such as a TGFβ2 receptor if the immunosuppressive agent is TGFβ2 or to express an antibody such as a single chain antibody that can specifically bind an immunosuppressive agent in the tumor cell (Duan et al., *Proc. Natl. Acad. Sci., USA* 91:5075-5079 (1994); Buonocore and Rose, *Proc. Natl. Acad. Sci., USA* 90:2695-2699 (1993), each of which is incorporated herein by reference). Expression in the tumor cell of such a binding protein can decrease the available immunosuppressive agent and, as a consequence, reduce or inhibit immunosuppression of a subject's immune response against a cancer.

Various assays to determine whether a subject's cancer cells express an immunosuppressive agent such as an immunosuppressive isoform of TGFβ are available and known to those skilled in the art. For example, a radioimmunoassay or enzyme linked immunosorbent assay can be used to detect a specific immunosuppressive agent in a serum or urine sample obtained from a subject. Other assays such as the mink lung epithelial cell assay can be used, for example, to identify TGFβ2 activity (see Example I). A biopsy of the tumor can be examined, for example, immunohistochemically for the expression of an immunosuppressive agent. In addition, the tumor cells can be evaluated by northern blot analysis, reverse transcriptase-polymerase chain reaction or other known methods (see, for example, Erlich, *PCR Technology: Principles and applications for DNA amplification* (Stockton Press 1989); Sambrook et al., *Molecular Cloning: A laboratory manual* (Cold Spring Harbor Laboratory Press 1989), each of which is incorporated herein by reference).

As disclosed herein, reducing or inhibiting the expression of an immunosuppressive agent by a tumor cell can attenuate the immunosuppressive effect of the agent and allow natural immune functions to work even in the presence of the endogenous circulating immunosuppressive agent. Thus, tumor cells that are genetically modified to reduce or inhibit the expression of an immunosuppressive agent can be useful as a vaccine to prevent or reduce the severity of a cancer in a subject by stimulating the subject's immune response against the cancer. For example, tumor cells that are genetically modified by homologous recombination gene knock-out of a gene encoding an immunosuppressive agent or by expressing an antisense nucleic acid sequence can be administered to a cancer patient to stimulate an immune response against the cancer and, thereby, reduce the severity of the cancer.

Such genetically modified tumor cells also can be used as a vaccine in a subject predisposed to developing a cancer in order to prevent a cancer from occurring in the subject. Such a vaccine can be produced, for example, by obtaining donor tumor cells that are substantially similar to the suspect cancer. Such donor tumor cells can be obtained, for example, from a donor subject having a cancer that is the same or substantially similar to the suspect cancer and genetically modifying the donor tumor cells to reduce or inhibit the expression of an immunosuppressive agent. The genetically modified donor tumor cells can be administered to the subject alone or in combination with an immunostimulatory agent such as an adjuvant or CE cells in order to stimulate the subject's immune response against the cancer.

In another embodiment, tumor cells are removed from a patient having a cancer and genetically modified to reduce or inhibit the expression of the immunosuppressive agent and further modified to express and secrete one or more immunostimulatory agents such as a cytokine or a known tumor antigen. The expression of an immunostimulatory agent in combination with the removal of the inhibitory effect of an immunosuppressive agent can augment positive immune functions in a subject. Such immune stimulation can effectively enhance the effect provided by reducing or inhibiting the expression of an immunosuppressive agent in a tumor cell. As a result, the genetically modified tumor cells can be particularly effective as a vaccine to prevent or reduce the severity of a cancer in a subject.

As used herein, the term "immunostimulatory agent" is used in its broadest sense to mean a molecule that can positively effect the immunoresponsiveness of a subject. For example, an immunostimulatory agent can be an adjuvant such as BCG (see Harlow and Lane, *Antibodies: A laboratory manual* (Cold Spring Harbor Laboratory Press 1988); Mishell and Shiigi, *Selected Methods in Cellular Immunology* (W. H. Freeman and Co. (1980)), each of which is incorporated herein by reference) or can be a gene product that can be administered locally or systemically to a subject or expressed in a cell. A tumor cell or a normal cell such as a fibroblast or an antigen presenting cell can be genetically modified to express an immunostimulatory agent that is a gene product. Immunostimulatory agents that are gene products are known in the art and include, for example, cytokines, the costimulatory B7 molecule (Baskar et al., *Proc. Natl. Acad. Sci., USA* 90:5687-5690 (1993); Townsend and Allison, *Science* 259:368-370 (1993); Tan et al., *J. Immunol.* 149:32217-3224 (1992), each which is incorporated herein by reference), autologous MHC class I and class II molecules (Plautz et al., *Proc. Natl. Acad. Sci., USA* 90:4645-4649 (1993); Hui et al., *Fems Microbiol. Immunol.* 2:215-221 (1990); Ostrand-Rosenberg et al., *J. Immunol.* 144:4068-4071 (1990), each of which is incorporated herein by reference), allogeneic histocompatability antigens such as HLA-B7 (Nabel et al., *Proc. Natl. Acad. Sci., USA* 90:11307-11311 (1993), which is incorporated herein by reference) and known tumor antigens (Finn, supra, 1993). For example, a tumor cell may not express an MHC class I or II molecule and, as a result, does not induce an optimal immune response. In this case, the MHC molecule can be an immunostimulatory agent, since, by expressing the MHC molecule in the tumor cell, the modified tumor cell can induce an immune response. Methods for determining whether a tumor cell expresses a particular immunostimulatory agent are known in the art and can be used to determine whether the tumor cell should be genetically modified to express a particular immunostimulatory agent.

A known tumor antigen can be particularly useful as an immunostimulatory agent. Various tumor antigens, including, for example, epithelial cell mucin, which is encoded by the MUC-1 gene, and the melanoma antigen, MZ2-E, which is encoded by the MAGE-1 gene, are associated with particular tumor cells (Finn, supra, 1993). Genetically modifying a tumor cell to express a known tumor antigen can be particularly useful when the tumor cells to be administered to a subject to be treated are not obtained from that subject. For example, it may not be possible to obtain a sufficient number of tumor cells from a cancer patient. In this case, donor tumor cells, which may not express one or more particular tumor antigens that are known to be expressed by the subject's cancer cells, can be obtained and can be genetically modified to express the particular tumor antigen. The donor tumor cells also will be genetically modified to reduce or inhibit the expression of an immunosuppressive agent. Upon administration of the genetically modified donor tumor cells to the subject, the subject's immune response against the cancer can be stimulated against the subject's cancer. Such genetically modified donor tumor cells also can be useful as a vaccine to prevent the development of a cancer in a subject predisposed to developing a particular cancer.

A cytokine can be useful as an immunostimulatory agent. As used herein, the term "cytokine" refers to a member of the class of proteins that are produced by cells of the immune system and positively regulate or modulate effector functions of the immune response. Such regulation can occur within the humoral or the cell mediated immune response and can modulate the effector functions of T cells, B cells, macrophages, antigen presenting cells or other immune system cells. Specific examples of cytokines include, for example, interleukin-1, interleukin-2, interleukin-3, interleukin-4, interleukin-5, interleukin-6, interleukin-7, interleukin-10, interleukin-12, interleukin-15, gamma-interferon, tumor necrosis factor, granulocyte colony stimulating factor and granulocyte-macrophage colony stimulating factor.

It is recognized that the expression of specific combinations of cytokines can be particularly useful for stimulating an immune response. For example, expression of gamma-interferon, IL-2 and interleukin-12 can stimulate T cells of the T helper-1 class, which are involved in the cellular immune response. Thus, it can be particularly useful to genetically modify tumor cells to reduce or inhibit the expression of one or more immunosuppressive agents, then to individually further modify aliquots of the cells to express gamma-interferon or IL-2 or interleukin-12. A composition comprising a combination of such genetically modified tumor cells can be administered to a subject to stimulate, in particular, a cellular immune response against the tumor cells.

In some cases, it can be difficult to obtain a sufficient number of cancer cells from a patient. Donor tumor cells that are genetically modified to reduce or inhibit the expression of an immunosuppressive agent and, if desired, further modified to express a known tumor antigen or a cytokine can be used to stimulate an immune response in such a patient. The genetically modified donor tumor cells also can be used to prevent a cancer in a normal subject or in a subject suspected of developing a cancer. Subjects that are predisposed to developing a cancer are known and can be identified using methods of genetic screening (Mao et al., Canc. Res. 54(Suppl.): 1939s-1940s (1994); Garber and Diller, Curr. Opin. Pediatr. 5:712-715 (1993). Such subjects can be predisposed to developing, for example, retinoblastoma, breast cancer or colon cancer.

A panel of genetically modified donor tumor cells, which can represent various histologic tumor types and express various known tumor antigens such as MZ2-E or mucin (see Finn, supra, 1993), can be prepared. Such a panel of genetically modified donor tumor cells can be maintained in a cell repository and are readily available for administration to a subject predisposed to developing a particular cancer. One or more tumor cell lines in such a panel can be used to stimulate a cancer patient's immune response against the patient's cancer. The skilled artisan can select an appropriate genetically modified donor tumor cell from the panel based, for example, on the histologic type of tumor the subject has or is predisposed to developing. If desirable, the artisan can further genetically modify a tumor cell obtained from such a panel depending on the particular characteristics of the cancer in the subject to be treated.

In still another embodiment, cancer cells are removed from a patient having a cancer, which is characterized, in part, by expressing an immunosuppressive agent, or donor tumor cells are obtained and the cells are genetically modified to reduce or inhibit the expression of the immunosuppressive agent. The genetically modified tumor cells then are combined with an immunostimulatory agent such as CE cells or an adjuvant to provide a composition that can be used to stimulate the cancer patient's immune response.

As used herein, the term "CE cell" or "cytokine-expressing cell" means a cell such as a fibroblast or an antigen presenting cell that is genetically modified to express and secrete one or more cytokines. As described above, the use of the cytokine gene therapy can augment positive immune functions in a subject in combination with the repression of the inhibitory effects of an immunosuppressive agent. A CE cell can be an autologous cell, which is obtained from the subject to be treated, or can be an allogeneic cell, which can be obtained, for example, from a donor subject or from a cell repository. It is recognized that cells to be used as CE cells must be examined to determine whether they express an immunosuppressive agent. If the cells express an immunosuppressive agent, they can be genetically modified to reduce or inhibit the expression of the agent using the methods described herein.

The invention also provides methods for preventing or reducing the severity of a cancer in a subject. Such a method can consist, for example, of stimulating the subject's immune response against the cancer by administering to the subject an effective amount of tumor cells that are substantially similar to the subject's cancer cells and that are genetically modified to prevent the expression of at least one immunosuppressive agent. In addition, the genetically modified tumor cells can be further modified to express and, if desirable, secrete an immunostimulatory agent or can be administered in combination with an immunostimulatory agent such as an adjuvant or an effective amount of a cytokine or of CE cells (see, for example, Khan et al., Pharm. Res. 11:2-11 (1994); Audibert and Lise, Immunol. Today 14:281-284 (1993), each of which is incorporated herein by reference).

As used herein, the term "effective amount" means an amount of a substance such as the genetically modified tumor cells, alone, or in combination with an immunostimulatory agent such as a cytokine or CE cells, that can stimulate an immune response to prevent or reduce the severity of a cancer in a subject. Such an effective amount can be determined using assays for determining the activity of immunoeffector cells following administration of the substance to the subject or by monitoring the effectiveness of the therapy using well known in vivo diagnostic assays as described below.

Figure 1A:
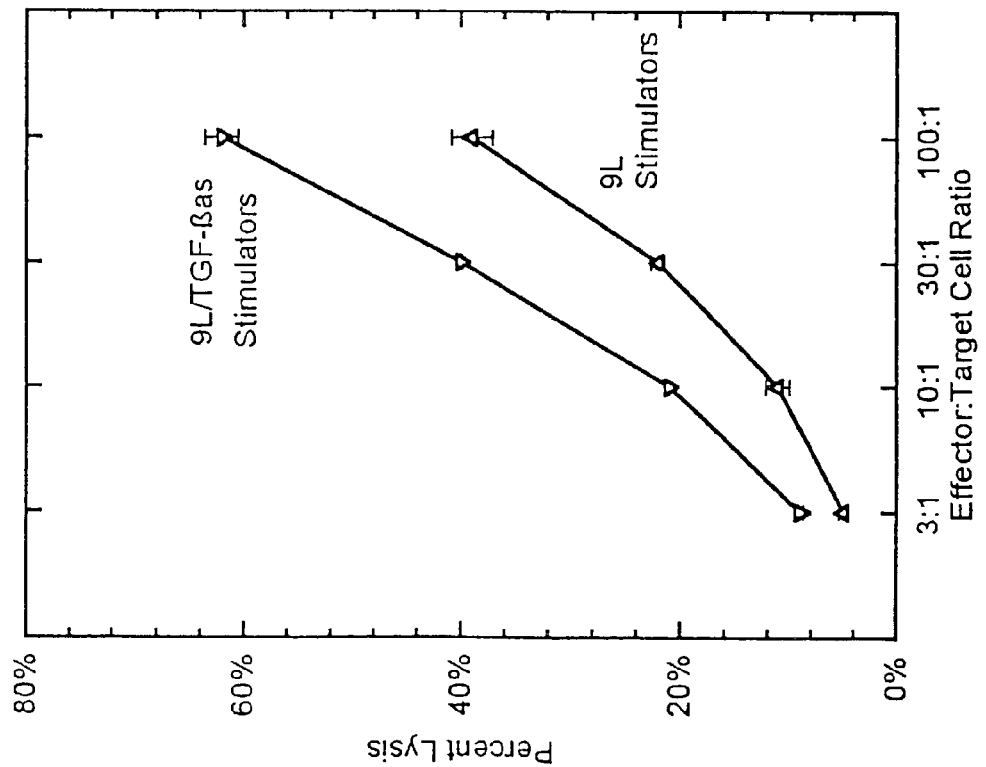

Based merely on in vitro experiments, it previously was suggested that the expression of TGFβ by a tumor cell inhibited immunoeffector functions against the tumor cell and that the inhibition of TGFβ expression in such tumor cells would render the cells more susceptible to immunoeffector cells (Hachimczak et al., J. Neurosurg. 78:944-951 (1993)). However, in vitro experiments to examine the immunoresponsiveness of immunoeffector cells against tumor cells following a particular treatment in vitro is not necessarily predictive of in vivo efficacy of the therapy. For example, rats were immunized with 9L gliosarcoma cells or 9L cells that had been genetically modified to express IL-2. When anti-tumor lytic activity of lymph node effector cells was examined in vitro, it was observed that in vitro-stimulated immunoeffector cells obtained from the rats immunized with the genetically modified gliosarcoma cells had greater cytolytic activity against target 9L gliosarcoma cells and greater natural killer cell activity than in vitro-stimulated immunoeffector cells obtained from unimmunized rats or rats immunized with unmodified 9L gliosarcoma cells (FIG. 1; see, also, Example I). If such in vitro results were predictive of in vivo efficacy, it would have been expected that immunization of rats with the IL-2 modified gliosarcoma cells would produce a greater immune response in the rats against 9L tumor cells. However, no significant difference in animal survival was observed in rats that were injected with $5 \times 10^3$ 9L gliosarcoma cells on days 1 and 2, then immunized twice per week for two weeks, beginning on day 5, with unmodified or with IL-2 modified 9L cells (see Table, below). Furthermore, previous in vitro studies showed that IL-2 and antibodies to TGFβ could significantly counteract TGFβ-induced depression in lymphocytes. However, when administered in vivo, these treatments resulted in either no anti-tumor effects or enhanced tumor growth (Gridley et al., Canc. Biother. 8:159-170 (1993)). Thus, in vitro results are not necessarily predictive of in vivo efficacy of a treatment.

Moreover, although expression of an antisense TGFβ nucleic acid sequence ("antisense TGFβ") in 9L gliosarcoma cells rendered the gliosarcoma cells immunogenic in vivo (see Table I, below), this was not the case in another animal model. Specifically, when antisense TGFβ was expressed in ovarian carcinoma cells, the genetically modified cells were no more immunogenic than the ovarian carcinoma cells administered alone or in combination with IL-2-producing CE cells (see FIG. 2). However, when a composition of ovarian tumor cells that had been genetically modified to express antisense TGFβ was administered to an experimental animal in combination with IL-2-producing CE cells, an immune response was stimulated against the tumor cells. Thus, as disclosed herein, the present invention provides methods for stimulating an immune response in a subject against the subject's cancer cells by immunizing the subject with tumor cells, which are genetically modified to prevent expression of an immunosuppressive agent, alone or in combination with an immunostimulatory agent.

The methods of tumor immunotherapy described herein utilize the genetic modification of tumor cells, which results in the reduction or inhibition of expression of one or more immunosuppressive agents by the tumor cells. Homologous recombination gene knock-out is particularly useful for reducing or inhibiting the expression of an immunosuppressive agent because it results in essentially total and permanent inhibition of expression of the immunosuppressive agent. Expression of an antisense nucleic acid sequence also can reduce or inhibit the expression of the immunosuppressive agent by the tumor cell. Regardless of the method for reducing or inhibiting expression of an immunosuppressive agent by a tumor cell, administration of the genetically modified tumor cells to a subject can stimulate a subject's immune response against a cancer. Thus, the disclosed methods are useful for reducing the severity of an existing tumor in a subject or for preventing the occurrence of a cancer in a subject predisposed to developing a cancer.

Tumor cells that show enhanced efficacy as an anti-tumor vaccine due to reduction or inhibition of expression of one or more immunosuppressive agents can be used therapeutically to treat a subject for a particular cancer. Tumor cells to be genetically modified can be obtained, for example, by biopsy from the subject having the cancer, which is characterized, in part, by expressing one or more immunosuppressive agents, and the tumor cells can be genetically modified to inhibit the expression of the immunosuppressive agent(s). Alternatively, as described above, donor tumor cells can be obtained and genetically modified. The genetically modified tumor cells then can be administered to the subject.

It is recognized that the tumor cells to be administered should be viable. However, administration of viable tumor cells to a subject requires that the tumor cells be inactivated so they do not grow in the subject. Inactivation can be accomplished by any of various methods, including, for example, by irradiation, which is administered to the cells at a dose that inhibits the ability of the cells to replicate but does not initially kill the tumor cells. Such viable tumor cells can present tumor antigens to the patient's immune system but cannot multiply and form new tumors.

Once the tumor cells are obtained from either the subject to be treated, a donor subject or an established cell line, the tumor cells are genetically modified such that expression of one or more immunosuppressive agents expressed by the tumor cell is reduced or inhibited (see Example II). Genetic modification is advantageous over other methods for inhibiting expression of the immunosuppressive agent in that it is efficient, specific for the intended gene product and can provide sustained inhibition of the expression of one or more immunosuppressive agents. As described above, methods of genetic modification include, for example, homologous recombination, which can permanently and completely inactivate the gene encoding the immunosuppressive factor, or expression of a ribozyme or an antisense nucleic acid sequence in a cell, which can inhibit or inactivate one or more steps involved in transcription, processing or translation of a nucleic acid molecule encoding the immunosuppressive agent. In addition, genetic modification can result in the expression in the tumor cell of a binding protein such as an antibody, which can specifically bind to an immunosuppressive agent and prevent the immunosuppressive activity.

Homologous recombination gene knock-out is an effective method of reducing or inhibiting expression of an immunosuppressive agent because of the complete and sustained inhibition of expression of the agent. In addition, antisense methods for reducing or inhibiting expression of an immunosuppressive agent are useful as disclosed herein. Antisense methods involve introducing into the tumor cell a nucleic acid sequence that is complementary to and can hybridize to the target nucleic acid molecule, which encodes the immunosuppressive agent, in a cell. An antisense nucleic acid sequence can be a chemically synthesized oligonucleotide, which can be introduced into the tumor cells by methods of transfection, or can be expressed from a vector, which can be stably introduced into the tumor cell using well known methods (see, for example, Sambrook et al., supra, 1989). One in the art would know that the ability of such a complementary nucleic acid sequence to hybridize to the target nucleic acid sequence depends, for example, on the degree of complementarity shared between the sequences, the length of the antisense nucleic acid sequence, which generally is an oligonucleotide that is at least ten nucleotides in length, and the GC content of the oligonucleotide (see Sambrook et al., supra, 1989).

A recombinant vector can be used to express an antisense nucleic acid sequence in the tumor cells. Such vectors are known or can be constructed by those skilled in the art and contain the expression elements necessary to achieve, for example, sustained transcription of an antisense nucleic acid sequence. Examples of vectors include viruses such as bacteriophages, baculoviruses and retroviruses and DNA viruses, cosmids, plasmids or other recombination vectors (Jolly, *Canc. Gene Ther.* 1:51-64 (1994), which is incorporated herein by reference). The vectors can also contain elements for use in procaryotic or eucaryotic host systems or, if desired, both systems. One of ordinary skill in the art would know which host systems are compatible with a particular vector. Vectors that result in high levels of sustained expression of the antisense nucleic acid sequences can be particularly useful.

Examples of useful viral vectors, for example, include adenovirus and adenovirus-associated vectors (see, for example, Flotte, *J. Bioenerg. Biomemb.,* 25:37-42 (1993) and Kirshenbaum et al., *J. Clin. Invest,* 92:381-387 (1993), each of which is incorporated herein by reference). Vectors are particularly useful when the vector contains a promoter sequence, which can provide constitutive or, if desired, inducible expression of a cloned nucleic acid sequence. Such vectors are well known in the art (see, for example, *Meth. Enzymol.*, Vol. 185, D. V. Goeddel, ed. (Academic Press, Inc., 1990), which is incorporated herein by reference) and available from commercial sources (Promega, Madison, Wis.).

Vectors can be introduced into the tumor cells by any of a variety of methods known in the art and described, for example, in Sambrook et al., supra, 1989, and in Ausubel et al., *Current Protocols in Molecular Biology*, John Wiley and Sons, Baltimore, Md. (1994), which is incorporated herein by reference. Such methods include, for example, transfection, lipofection, electroporation and infection with recombinant vectors or the use of liposomes. Introduction of nucleic acids by infection is particularly advantageous in that it can be effective in vitro or in vivo. Higher efficiency can also be obtained due to their infectious nature. Moreover, viruses are very specialized and typically infect and propagate in specific cell types. Thus, their natural specificity can be used to target the antisense vectors to specific tumor cell types in a biopsy culture, which may be contaminated with other cell types. Viral or non-viral vectors can also be modified with specific receptors or ligands to alter target specificity through receptor mediated events. The use of retroviral vectors for the expression of antisense sequences is described below.

A nucleic acid molecule also can be introduced into a tumor cell using methods that do not require the initial introduction of the nucleic acid sequence into a vector. For example, a nucleic acid sequence useful for inactivating a gene in a tumor cell such as a gene encoding an immunosuppressive isoform of TGFβ can be introduced into a tumor cell using a cationic liposome preparation (Morishita et al., *J. Clin. Invest.*, 91:2580-2585 (1993), which is incorporated herein by reference; see, also, Nabel et al., supra, 1993)). In addition, a nucleic acid sequence can be introduced into a tumor cell using, for example, adenovirus-polylysine DNA complexes (see, for example, Michael et al., *J. Biol. Chem.*, 268:6866-6869 (1993), which is incorporated herein by reference). Other methods of introducing a nucleic acid sequence into a tumor cell such that the nucleic acid can be expressed or can result in the reduction or inhibition of expression of a gene product are well known and described, for example, by Goeddel, supra, 1990).

Nucleic acid sequences encoding various immunosuppressive and immunostimulatory agents have been cloned and are available for use (GenBank). Nucleic acid sequences encoding, for example, cytokines such as various interleukins, gamma-interferon and colony stimulating factors are available from the American Type Culture Collection (see ATCC/NIH Repository Catalogue of Human and Mouse DNA Probes and Libraries, 6th ed., 1992) or are available commercially (Amgen, Thousand Oaks, Calif.; see, also, Patchen et al., *Exptl. Hematol.*, 21:338-344 (1993); Broudy et al., *Blood*, 82:436-444 (1993), each of which is incorporated herein by reference). Similarly, nucleic acid sequences encoding immunosuppressive agents such as various immunosuppressive isoforms of TGFβ are available to those in the art.

In addition, a nucleic acid sequence encoding an immunosuppressive agent, for example, can be obtained and modified such that, following homologous recombination with the target gene in the tumor cell, the immunosuppressive agent is not expressed. Nucleic acid sequences encoding various immunosuppressive agents or immunostimulatory agents also can be obtained using, for example, the polymerase chain reaction, provided some information of the nucleic acid sequence encoding the agent is known. Other methods such as cloning also can be used to isolate a desired nucleic acid sequence encoding an immunosuppressive or immunostimulatory agent.

Selectable marker genes encoding, for example, a polypeptide conferring neomycin resistance ($Neo^R$) also are readily available and, when linked to a nucleic acid sequence or incorporated into a vector, allows for the selection of cells that have successfully incorporated the desired nucleic acid sequence, which can inactivate a target gene by homologous recombination, encode an antisense nucleic acid sequence or encode an immunostimulatory agent. Other selectable markers known to those in the art of gene transfer also can be used to identify tumor cells that have been genetically modified, for example, by homologous recombination to reduce or inhibit the expression of one or more immunosuppressive factors.

A "suicide" gene also can be incorporated into a vector so as to allow for selective inducible killing of a genetically modified tumor cell following stimulation of a subject's immune response. A gene such as the herpes simplex virus thymidine kinase gene (TK) can be used as a suicide gene to provide for an inducible destruction of the tumor cells. For example, when the tumor cells are no longer useful, a drug such as acyclovir or gancyclovir can be administered to the subject. Either of these drugs selectively kills cells expressing a viral TK, thus eliminating the implanted genetically modified tumor cells. Additionally, a suicide gene can encode a non-secreted cytotoxic polypeptide and can be linked to an inducible promotor. If destruction of the tumor cells is desired, the appropriate inducer of the promotor is administered so that the cytotoxic polypeptide is expressed.

Numerous methods are available for transferring nucleic acid sequences into cultured cells, including the methods described above. In addition, a useful method can be similar to that employed in previous human gene transfer studies, where tumor infiltrating lymphocytes (TILs) were modified by retroviral gene transduction and administered to cancer patients (Rosenberg et al., *New Engl. J. Med.* 323:570-578 (1990)). In that Phase I safety study of retroviral mediated gene transfer, TILs were genetically modified to express the Neomycin resistance ($Neo^R$) gene. Following intravenous infusion, polymerase chain reaction analyses consistently found genetically modified cells in the circulation for as long as two months after administration. No infectious retroviruses were identified in these patients and no side effects due to gene transfer were noted in any patients. These retroviral vectors have been altered to prevent viral replication by the deletion of viral gag, pol and env genes. Such a method can also be used ex vivo to transduce tumor cells taken from a subject with cancer.

When retroviruses are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. Hence, all retroviral vector supernatants used to infect patient cells will be screened for replication competent virus by standard assays such as PCR and reverse transcriptase assays.

Approximately $1 \times 10^7$ tumor cells are required for immunization, depending, for example, on the number of times the composition is to be administered and the level of response desired. The tumor cells can be mixed with an appropriate adjuvant or with a pharmacologically acceptable solution such as physiological saline or the like for administration, which can be accomplished by any of various methods such as subcutaneous or intramuscular injection or any manner acceptable for immunization. Pharmacologically acceptable solutions useful for immunization are known in the art (see, for example, Khan et al., supra, 1994; Audibert and Lise, supra, 1993; Mishell and Shiigi, supra, 1980). In addition, various methods of administration can be used and are known to those skilled in the art. Administration can be at a body location other than an active tumor site or, if desired, at the site of a tumor in a cancer patient or can be in a subject predisposed to developing a cancer.

One skilled in the art would know that the effectiveness of therapy can be determined by monitoring immune functions in the patient. For example, the cytolytic activity of immune effector cells against the patient's cancer cells can be assayed using the methods described in Example I. In addition, the size or growth rate of a tumor can be monitored in vivo using methods of diagnostic imaging. By monitoring the patient during therapy, the therapist would know whether to maintain, for example, therapy using tumor cells that are genetically modified to prevent expression of an immunosuppressive agent or whether it is more desirable to use a combination therapy, which can reduce or prevent the expression of an immunosuppressive agent and, at the same time, can provide an immunostimulatory agent. Such combined gene therapy can exhibit superior efficacy because not only are the immunosuppressive functions depressed but the stimulatory functions of the immune system are enhanced. This combined approach is particularly useful when separate inhibition of an immunosuppressive agent or stimulation of the immune response using an immunostimulatory agent provides only moderate effects when used alone.

Where combined therapy is used, tumor cells expressing, for example, an antisense nucleic acid sequence to an immunosuppressive agent can be further modified to express one or more immunostimulatory agents such as cytokines. The tumor cells should be modified so that a known number of cells in the composition secrete, for example, appropriate cytokine levels, which can induce anti-tumor immunity without producing substantial systemic toxicity in a subject. Alternatively, the genetically modified tumor cells can be administered in combination with CE cells, which express and secrete a defined level of cytokines. The expression of an appropriate level of a cytokine allows administration of an effective amount of the composition, while minimizing the likelihood of adverse side effects as were observed using previously described methods of systemic administration of greater than physiological levels of the cytokines.

As with the tumor cells modified with antisense described previously, tumor cells that express an antisense nucleic acid and an immunostimulatory agent or the combination of tumor cells that express an antisense nucleic acid sequence for an immunosuppressive agent and an immunostimulatory agent such as a cytokine or CE cells can be formulated for injection in any manner known in the art as being acceptable for immunization. Because it is important that the tumor cells and, if used, CE cells remain viable, the formulations are compatible with cell survival. It is recognized that contamination of a composition of the invention can focus the immune response on undesired antigens and, therefore, should be avoided by practicing aseptic techniques.

It is understood that modifications that do not substantially affect the activity of the embodiments of this invention also are included within the invention provided herein. Accordingly, the following examples are intended to illustrate but not limit the present invention.

Example I

Immunosuppressive Effect of TGFβ in Tumor Cells

This example demonstrates that various tumor cell lines produce an immunosuppressive isoform of TGFβ.

A murine ovarian teratoma cell line, MOT D3-17-5 (MOT), a human glioblastoma cell line, GT-9, and a rat gliosarcoma cell line, 9L, were used to assess the immunosuppressive effects of TGFβ. Expression of TGFβ was determined by measuring the ability of TGFβ to suppress the growth of mink Mv-1-Lu lung epithelial cells (ATCC CCL64; Rockville Md.; Ogawa and Seyedin, *Meth. Enzymol.* 198:317-327 (1991), which is incorporated herein by reference). Briefly, mink lung epithelial cells are grown in DMEM containing 10% FCS, 50 U/ml penicillin, 50 µg/ml streptomycin, nonessential amino acids and L-glutamine until near confluency. Cells were trypsinized and collected by centrifugation at 800× g for 2 min, then resuspended in culture medium at 20,000 cells/ml. The cells were plated on 96-well microtiter plates at 1000 cells/well (50 ul/well) and allowed to attach for 30 min.

Fifty µl conditioned supernatant from the various cultured tumor cell lines were added in triplicate to well containing mink lung epithelial cells. Plates were incubated for 4 days at 37° C. in an atmosphere containing 10% $CO_2$. Wells were rinsed with phosphate buffered saline (PBS), then filled with 100 ul 0.1 M sodium acetate (pH 5.5)/0.1% Triton X-100/100 mM p-nitrophenylphosphate and the plates were incubated for 2 hr at 37° C. Color development was generated by the addition of 10 ul 1.0 N NaOH and the absorbance at 405 nm, which is proportional to the number of cells, was determined. Supernatants obtained from the MOT, GT-9 and 9L tumor cell cultures inhibited mink lung epithelial cell proliferation in a dose-dependent manner, indicating that each of these tumor cell lines secrete biologically active TGFβ (not shown).

The mink lung epithelial cell assay also can be performed using mink lung epithelial cells that are pulsed for 4 hr with 0.5 µCi $^3$H-thymidine. In this case, the number of counts is proportional to the number of proliferating cells, which decreases in the presence of increasing amounts of TBFβ.

The specific isoform of TGFβ in a sample can be determined using anti-TGFβ antibodies. However, since TGFβ exists in a cell in an active form and in an inactive form and since anti-TGFβ antibody only reacts with active TBFβ, in some experiments, TGFβ can be activated by acidification so that total TGFβ in the sample can be determined. Prior to addition of a cell supernatant to the mink lung epithelial cells, the supernatants either are left untreated, in order to measure the amount of active TGFβ secreted, or are acidified to activate TBFβ. The culture supernatant is acidified by adjusting to pH 2-3 with HCl, incubated for 30 min, then neutralized with NaOH. Antibodies specific for TGFβ1 or TGFβ2 (R & D Systems; Minneapolis Minn.) are added to some wells to determine specificity. Known concentrations of TGFβ are used to generate a standard curve.

To determine the inhibitory effect of TGFβ on immunoresponsiveness using the 9L tumor model, F344 rats were immunized subcutaneously with $2 \times 10^6$ irradiated (5000 cGy) unmodified 9L gliosarcoma cells or 9L cells that had been transduced with LNCX-IL2, which is a retroviral vector that expresses IL-2. The LNCX-IL2 vector was constructed by inserting a human IL-2 cDNA containing the rat preproinsulin secretory signal (Cullen, *DNA* 7:645-650 (1988), which is incorporated herein by reference) into LNCX, which contains a cytomegalovirus (CMV) promotor and was packaged in PA317 cells (Miller and Buttimore, *Mol. Cell Biol.* 6:2895-2902 (1986), which is incorporated herein by reference).

For transduction, 9L cells were seeded at a density of $2 \times 10^6$ cells/T-75 flask (20% confluency). After the cells attached to the flask, the supernatant was removed and the cultures were washed once with PBS, then incubated at 37° C. in serum-free medium containing 20 µg/ml DEAE-dextran. After 30 min, the DEAE-dextran was removed and replaced with 10 ml medium containing LNCX-IL2 and 8 µg/ml polybrene. To provide adequate nutrient levels during the transduction period, the retroviral supernatant was diluted 1:1 with fresh medium before being adjusted to 8 µg/ml polybrene. The virus supernatant was removed from cultures after 6 to 24 hr and replaced with fresh medium. Selection of transductants was initiated with 50-400 µg/ml active G418 beginning the next day.

Fourteen days following immunization of the rats with unmodified or transduced 9L gliosarcoma cells, the lymph nodes were removed and lymph node effector cells were isolated, then incubated for 5 days in DMEM supplemented with 10% fetal calf serum (FCS) and 50 U/ml recombinant human IL-2. Irradiated 9L cells (5000 cGy) were added at an effector cell:stimulator cell ratio of 30:1 to duplicate flasks. Turkey anti-TGFβ antiserum was added to one flask.

After 5 days, the splenocytes or lymph node cells were harvested and assayed for lytic activity in vitro by a four hour chromium release assay using $^{51}$Cr-labeled 9L cells as target cells (Shawler et al., *J. Clin. Lab. Anal.* 1:184-190 (1987); Dillman et al., *J. Immunol.* 136:728-731 (1986), each of which is incorporated herein by reference). In addition, $^{51}$Cr-labeled A2T2C4 cells, which are a rat natural killer- (NK-) sensitive cell line, (Gallimore et al., *J. Mol. Biol.* 89:49-72 (1974), which is incorporated herein by reference) were used as targets to test for NK activity.

The results of these assays demonstrated that cytotoxic T cell activity and NK cell activity was significantly greater in rats immunized with 9L cells that had been genetically modified to express IL-2 as compared to unmodified 9L cells. The addition of neutralizing concentrations of anti-TGFβ2 antibody to the in vitro stimulation portion of the assay caused about a two-fold increase in the killing of 9L gliosarcoma target cells at an effector cell:target cell ratio of 100:1 (not shown). However, no significant increase in animal survival time was observed in rats immunized with the genetically modified 9L cells as compared to unimmunized rats or rats immunized with 9L cells transduced with a control vector.

The results of these experiments indicate that TGFβ expression can reduce or prevent an immune response to a cancer in vivo. In addition, the results indicate that the effectiveness of a immunostimulatory agent such as IL-2 at inducing immunoresponsiveness as determined using an in vitro assay is not necessarily predictive of the ability of the agent to stimulate an immune response in vivo.

Example II

Effect of Antisense TGFβ Expression on Immunogenicity of Tumor Cells

This example demonstrates that expression of an antisense TGFβ nucleic acid sequence in a tumor cell, which is characterized, in part, by producing TGFβ, allows for the induction of an immune response against the tumor cells in vivo.

A. 9L Gliosarcoma Cells

To analyze the systemic anti-tumor effects of inhibiting an immunosuppressive agent such as TBFβ, 9L gliosarcoma cells were transfected with a vector expressing an antisense TGFβ nucleic acid sequence. A nucleic acid sequence encoding antisense TGFβ2 was inserted into the pCEP4 vector (Invitrogen; San Diego Calif.). The TGFβ2 nucleic acid sequence was obtained from pSTGFbeta2, which contains a cDNA encoding TGFβ2 that was isolated from African green monkey kidney cells (Hanks et al., *Proc. Natl. Acad. Sci., USA* 85:79-82 (1988), which is incorporated herein by reference; ATCC #77322; Rockville Md.)

pSTGFbeta2 was digested with XhoI and HindIII to release a 957 base pair (bp) fragment, which contains 870 bp encoding the 5' end of TGFβ2. The expression vector pCEP4 also was digested with HindIII and XhoI. The restriction enzyme digested products were fractionated by electrophoresis in an agarose gel, the bands corresponding to the linearized pCEP4 vector and the 957 bp TGFβ2 sequence were removed and the nucleic acids were released from the gel slices using the routine glass powder method (see Sambrook et al., supra, 1989). The isolated vector and the TGFβ2 fragment were ligated overnight at 16° C. and the ligation product was used to transform XL-1 bacteria. A clone containing a plasmid having the appropriate sized band was isolated and used for large scale DNA preparation (pCEP4/TGFB2). Ligation of the XhoI/HindIII digested 957 bp TGFβ2 fragment into pCEP4 placed the TGFβ2 fragment in a reverse orientation with respect to the CMV promotor in pCEP4.

pCEP4/TGFB2, which encodes antisense TGFβ2, was transfected using the calcium phosphate method into 9L gliosarcoma cells and into 9L cells that were transduced to contain an IL-2 expressing retroviral vector (91/LNCX/IL2 cells) or a control retroviral vector (9L/LXSN/O cells). The transfected cells were cultured in presence of hygromycin, which selects for cells containing pCEP4/TGFB2, until colonies appeared.

TGFβ secretion by the transfected cell lines was determined using the mink lung epithelial cell assay. Cells that contained pCEP4/TGFB2 were negative for TGFβ activity (not shown). These results indicate that an antisense TGFB2 produced in the transfected cells can hybridize with a nucleic acid molecule encoding TGFβ in the cell and reduce or inhibit the expression of TGFβ.

The cytolytic activity of immune effector cells in vitro was examined in a 4 hour $^{51}$Cr release assay as described above. Briefly, lymph nodes from rats immunized with unmodified 9L cells or with 9L cells modified to express and secrete IL-2 were collected and lymph node cells cultured for 5 days in presence of 50 BRMP units IL-2 per ml and either unmodified 9L cells or antisense TGFB2 modified 9L-cells. Cytotoxicity of the effector cells was determined in a 4 hour $^{51}$Cr release assay using unmodified 9L cells as targets. As shown in FIG. 1, lymph node cells stimulated in vitro by 9L cells expressing antisense TGFB2 exhibited significantly increased cytolytic activity against 9L cells than effector cells cultured in the presence of unmodified 9L cells.

The effect of immunization on the survival of rats having intracranially implanted 9L gliosarcoma cells also was determined. $5 \times 10^3$ 9L cells were implanted into the forebrain of rats on days 1 and 2. Beginning on day 5, the rats were immunized four times on a twice per week schedule with either saline, 9L cells transduced with a control vector, 9L cells genetically modified to express antisense TGFβ2, 9L cells transduced to express IL-2 or 9L cells genetically modified to express antisense TGFβ2 and IL-2.

As shown in the Table, immunization with unmodified 9L cells (control) or 9L cells expressing IL-2 resulted in survival of 30% of the immunized animals. Significantly, the survival of rats immunized with 9L cells transduced to express IL-2 was the same as rats immunized with unmodified 9L cells. In contrast, 100% survival was observed in rats immunized with 9L cells that express antisense TGFβ2, regardless of whether the 9L cells also expressed IL-2. These results indicate that the expression of antisense TGFβ2 in a tumor cell that expresses TGFβ can render the tumor cells immunogenic in tumor bearing host.

A retroviral vector encoding an antisense TGFβ2 also was constructed using the retroviral parental plasmid pLHCX, which is a modification of pLNCX in which the gene conferring neomycin drug resistance is replaced with a gene conferring hygromycin resistance. pLHCX was digested with HindIII and HpaI and the linearized plasmid was purified from an agarose gel as described above. pSTGFbeta2 was digested with XhoI and the XhoI end was blunted by treatment with Klenow fragment of *E. coli* DNA polymerase I in presence of all four deoxynucleotides. After phenol

TABLE

Effect of Immunization with IL-2 and TGF-βas
Modified Tumor Cells on Survival of Rats with
Intracranially Implanted Tumors

| Inoculum | Antigen dose | Units IL-2 per 24 hr | Animals surviving (11 weeks) |
|---|---|---|---|
| Unimmunized | — | 0 | 0/10 |
| 9L/Vector (control) | $2.5 \times 10^5$ | 0 | 3/10 |
| 9L/IL-2 | $2.5 \times 10^3$ | 50 | 3/10 |
| 9L/TGF-βas | $2.5 \times 10^5$ | 0 | 6/6 |
| 9L/TGF-βas/IL-2 | $2.5 \times 10^3$ | 50 | 7/7 |

- $5 \times 10^3$ tumor cells were implanted into the forebrain of rats on days 1 & 2. Beginning on day 5 animals were immunized 4 times on a twice a week schedule extraction and ethanol precipitation the linearized pSTGF-beta2 was digested with HindIII to release a 957 bp band, which contains 870 bp of the 5' end of the TGFβ2 cDNA. Transduction of the tumor cells was performed as described above and transduced tumor cells selected by growth in the presence of hygromycin.

Successful inhibition of TGFβ expression in the modified tumor cells was confirmed by determining TGFβ levels in the supernatants of the modified cell cultures using the mink cell assay described above. Transgene expression also can be assessed at the RNA level using RNA isolated by the method of Chomczynski and Sacchi (*Anal. Biochem.*, 162:156-159 (1987), which is incorporated herein by reference). Briefly, transduced cells are lysed using lysis buffer containing 4 M guanidinium thiocyanate, then the lysate is extracted using water-saturated phenol and chloroform to remove the cellular proteins. RNA is isolated by isopropanol precipitation and used to synthesize first strand cDNA for mRNA PCR analysis or used for northern blot analysis. First strand cDNA is synthesized using the first strand Cycle™ kit according to the manufacturer's recommendation (Invitrogen; San Diego Calif.).

In order to determine the level of in vitro transgene expression, RNA is isolated from cells that are recovered following subcutaneous injection into rats and is subjected to PCR analysis (Mullis and Faloona, *Meth. Enzymol.*, 155:335-350 (1987), which is incorporated herein by reference). First strand cDNA is synthesized by the standard primer extension of oligo dT-primed mRNA using reverse transcriptase. PCR amplification is performed in 100 µg/ml nuclease-free BSA, 35 200 µM each DATP, dGTP, dCTP and dTTP, template-DNA, 100 pmol each primer and 2.5 units Taq polymerase. Temperatures and cycle numbers that minimize fortuitous bands are selected for these PCR amplifications (Hickey et al., *J. Exp. Med.* 176:811-187 (1992), which is incorporated herein by reference).

Transcription efficiency is determined by northern blot analysis. Total RNA or mRNA aliquots are fractionated by electrophoresis in an agarose gel containing formaldehyde, then transferred to a nylon membrane (Fakhrai and Mins, *J. Biol. Chem.* 267:4023-4029 (1992); Morrissey et al., *Cell* 50:129-135 (1978), each of which is incorporated herein by reference). RNAse activity is inhibited by treating all glassware and solutions with diethylpyrocarbonate.

Following transfer, the filters are dried in a vacuum oven at 80° C., prehybridized and hybridized in a cocktail containing 5xDenhardt's solution, 100 mM sodium phosphate (pH 7.5), 0.5% SDS, 1 mM sodium pyrophosphate, 100 µM ATP and 50% formamide (see Sambrook et al., supra, 1989). Prehybridization and hybridization are performed at 42° C. Following hybridization, the filters are washed twice for 5 min each at room temperature with 2xSSC/0.5% SDS, then twice for 1 hr each at 65° C. with 0.1xSSC/0.1% SDS (1xSSC=0.15 M NaCl, 0.015 M sodium acetate) and exposed to Kodak XAR-5 Film. Endogenous and antisense TGFβ transcripts are detected using riboprobes, which can hybridize to the RNA on the filters.

Sense and antisense riboprobes are prepared by isolating the 1540 bp TGFβ2 cDNA insert in pSTGFB2 and subcloning the insert into pGEM-5ZF (Promega; Madison Wis.). The sense or antisense strands are produced from the appropriate RNA polymerase promotor, SP6 or T7, as described by the manufacturer. These full length RNA probes are used to detect sense and antisense TGFβ nucleic acid sequences. Alternatively, unique restriction sites within the TGFβ2 cDNA can be used to linearize pSTGFB2 and shorter, more specific sense or antisense RNA probes can be synthesized.

For DNA analysis, 20 µg aliquots of genomic DNA isolated from recovered cells are digested with various restriction enzymes and size fractionated on a 1% agarose slab gel in 40 mM Tris-acetate/2 mM EDTA. Following electrophoresis, the DNA transferred to nylon membrane using 10xSSC (Sambrook et al, supra, 1989). The blots are hybridized with specific labeled probes as described above to detect the transgene of interest.

B. Murine Ovarian Teratoma Cells

The results described above indicate that inhibition of TGFβ expression in 9L gliosarcoma cells can enhance a host's systemic immune response to the tumor cells, regardless of whether an immunostimulatory agent such as IL-2 is present during immunization. However, different results were observed when murine ovarian teratoma cells were examined.

Murine ovarian teratoma (MOT) cells, which produce high levels of TGFβ, cannot easily be grown in tissue culture and, therefore, cannot be genetically modified using a retroviral vector in vitro. Fresh MOT cells were isolated from murine ascite's and were transfected with pCEP4/TGGβ2, which expresses antisense TGFβ2, by electroporation. Expression of TGFβ in MOT cells and in MOT cells that were genetically modified to express antisense TGFβ2 was assayed using the mink lung epithelial cell assay. Endogenous TGFβ transcripts are monitored by northern blot analyses utilizing sense and antisense specific riboprobes, as described above.

Packaged retroviral vector LNCX/IL2 was used to transduce allogeneic fibroblasts obtained from BALB/c mice to produce CE cells. Several transduced clones were selected and expression of IL-2 was determined using a commercially available kit (T-Cell Diagnostics, Cambridge, Mass.). The antisense TGFβ2 modified MOT cells were mixed with CE cells and were injected into C3H mice. In control experiments, unmodified MOT cells, alone, or in combination with CE cells, or MOT cells genetically modified to express antisense TGFβ2, alone, were injected into C3H mice. Fourteen days later, $1 \times 10^4$ live MOT cells were injected intraperitoneally into the mice and tumor growth was monitored.

In contrast to the results observed for 9L gliosarcoma cells, immunization only with MOT cells that were genetically modified to express antisense TGFβ2 did not significantly increase the survival of the animals (FIG. 2). All of the unimmunized mice and the mice receiving MOT cells expressing antisense TGFβ2 were dead within four weeks. Immunization with unmodified MOT cells or with a combination of MOT cells and CE cells resulted in survival of one or two mice, respectively. However, these results were not significantly different from results obtained for the unimmunized mice. In contrast, immunization with a combination of CE cells and MOT cells expressing antisense TGFβ resulted in survival of five of seven mice after 42 days (FIG. 2).

The results of the experiments described herein indicate that, in some cases, immunization with a tumor cells that are genetically modified to prevent the expression of an immunosuppressive agent such as tumor cells modified to express an antisense TGFβ2 combined with an immunostimulatory agent such as IL-2 can significantly increase the survival of a host to a cancer. In particular, the results indicate that there is no detrimental effect of using the combined treatment, which prevents or inhibits expression of an immunosuppressive agent and provides an immunostimulatory agent.

Although the invention has been described with reference to the above examples, it is understood that various modifications can be made without departing from the spirit of the invention. Accordingly, the invention is limited only by the following claims.

We claim:

1. A method of stimulating an immune response against a cancer, comprising administering to a subject an effective amount of tumor cells that are substantially similar to the subject's cancer cells and that are genetically modified to provide an inhibitor of the expression of at least one immunosuppressive agent, wherein said inhibitor is an antisense molecule to the sequence encoding the immunosuppressive agent, wherein said tumor cells are the same histologic type as the subject's cancer cells and express at least one antigen that is the same as an antigen expressed by the subject's cancer cells wherein said immunosuppressive agent is TGFβ, fibronectin, tenascin, p15E or lymphocyte blastogenesis inhibitory factor.

2. The method of claim 1, wherein said tumor cells are derived from said subject.

3. The method of claim 1, wherein said tumor cells are donor tumor cells.

4. The method of claim 1, wherein said tumor cells are carcinoma cells, glioma cells, sarcoma cells, lymphoma cells, melanoma cells or leukemia cells.

5. The method of claim 1, further comprising administering an immunostimulatory agent to said subject.

6. The said method claim 5, wherein said immunostimulatory agent is a cytokine.

7. The method of claim 6, wherein said cytokine is interleukin-1, interleukin-2, interleukin-3, interleukin-4, interleukin-5, interleukin-6, interleukin-7, interleukin-12, interleukin-15, gamma-interferon, tumor necrosis factor, granulocyte colony stimulating factor or granulocyte-macrophage colony stimulating factor.

8. The method of claim 6, wherein said cytokine is interleukin-2.

9. The method of claim 5, wherein immunostimulatory agent is cytokine-expressing cells.

* * * * *